United States Patent [19]

Cordon

[11] 4,038,380
[45] July 26, 1977

[54] CALCIUM META SILICATE AS DENTAL POLISHING AGENT

[75] Inventor: Martin Cordon, Highland Park, N.J.

[73] Assignee: Colgate-Palmolive Company, New York, N.Y.

[21] Appl. No.: 686,848

[22] Filed: May 17, 1976

[51] Int. Cl.² ............................................. A61K 7/16
[52] U.S. Cl. ...................................... 424/49; 51/308; 51/309 R
[58] Field of Search ................................ 51/308–309; 424/49–58

[56] References Cited

U.S. PATENT DOCUMENTS

| | | | |
|---|---|---|---|
| 2,010,910 | 8/1935 | Atkins | 424/49 |
| 2,059,396 | 11/1936 | Ribert | 424/49 |
| 2,820,000 | 1/1958 | Menzies | 424/49 |
| 2,844,444 | 7/1958 | Jordan | 23/313 |
| 2,873,181 | 2/1959 | Hanford | 51/308 X |
| 2,977,206 | 3/1961 | Sheets | 51/308 |
| 3,060,098 | 10/1962 | Gershon | 424/49 |
| 3,151,027 | 9/1964 | Cooley et al. | 424/52 |
| 3,257,282 | 1/1966 | Muhler | 424/52 |
| 3,573,886 | 4/1971 | Goetzinger et al. | 51/308 |
| 3,803,301 | 4/1974 | Cordon et al. | 424/49 |
| 3,804,946 | 4/1974 | Harrison et al. | 424/54 |
| 3,929,987 | 12/1975 | Colodney et al. | 424/52 |
| 3,935,306 | 1/1976 | Roberts et al. | 424/49 |

FOREIGN PATENT DOCUMENTS

| | | |
|---|---|---|
| 2,426,110 | 1/1975 | Germany |
| 207,769 | 12/1967 | U.S.S.R. |

OTHER PUBLICATIONS

Gershon et al., "Dentifrices", Chap. 14, vol. I, 2nd Ed. (1972), pp. 424–434, 461–476, 482–483, of Balsam et al., (Ed.) Cosmetics Science & Technology, Wiley-Interscience, N.Y., N.Y.

*Primary Examiner*—Shep K. Rose
*Attorney, Agent, or Firm*—Robert L. Stone; Murray M. Grill; Herbert S. Sylvester

[57] ABSTRACT

Dentifrice possessing enhanced cleaning and polishing characteristics containing as the essential cleaning and polishing agent calcium meta silicate.

7 Claims, No Drawings

CALCIUM META SILICATE AS DENTAL POLISHING AGENT

This invention relates to a dentifrice having superior cleaning and polishing characteristics containing calcium meta silicate ($CaSiO_3$) as the sole cleaning and polishing agent or as part of an abrasive system.

It is desirable to use dentifrices in the daily brushing and cleaning of teeth to provide abrasive action. It has been difficult to select suitable abrasives to afford maximum removal of difficult stains and debris without damaging the enamel surfaces of the teeth.

The function of an abrasive substance in formulations intended for use in the oral cavity is to remove various deposits, including pellicle film from the surface of the teeth. Pellicle film is a tightly adherent film which often contains brown or yellow pigments and imparts an unsightly appearance to the teeth. An advantageous abrasive material for incorporation into dental formulations should maximize film removal without causing undue abrasion to the hard tooth tissues. The typical soft abrasive used in dental compositions, such as dicalcium phosphate and calcium pyrophosphate, although not unduly abrasive to tooth tissue, are not as effective as the hard abrasives in removing these undesirable deposits from the teeth. However, hard abrasives can present serious problems when present in dental preparations since their outstanding abrasive characteristics can cause undue abrasion to the oral hard tissues (enamel, dentin and cementum).

It is now been found that the use of calcium meta silicate as the sole abrasive, or in conjunction with other abrasives, yields a dentifrice which effects superior polishing action without causing excess enamel abrasion normally associated with hard abrasives.

Accordingly, a dentifrice possessing superior polishing action without increasing the enamel abrasivity thereof can be formulated containing calcium meta silicate as the essential polishing and cleaning agent.

Ground glass (calcium silicate) has been cited in the prior art (U.S. Pat. Nos. 3,767,791 and No. 3,151,027) as a hard abrasive constituent in a dentifrice composition. However, said commercial silicate glass is not pure calcium silicate, but is primarily a source of silica and is composed of about 72% $SiO_2$, 15% $Na_2O$, 0-1% $K_2O$, 9% CaO, 1% $Al_2O_3$, and 3% MgO, as defined in the Encyclopedia of Chemical Technology by R. E. Kirk and D. F. Othmer, *Vol.* 7, Interscience, New York, 1951. On the contrary, the calcium meta silicate of this invention is a naturally occurring, brilliant white, substantially pure calcium meta silicate (e.g., about 98% pure) having the chemical formula $CaSiO_3$, a molecular weight of 116, and is composed of about 50.9% $SiO_2$ and about 46.9% CaO, with minor amounts of impurities. These impurities may include about 0.55% FeO, 0.25% $Al_2O_3$, 0.10 MnO, 0.10% MgO, 0.05 $TiO_2$, and 0.90 moisture (by loss on ignition). Calcium meta silicate should be in particulate form with a mean particle size typically in the range of about 2 microns to 15 microns, and preferably about 5 to 15 microns. It is preferable that at least about 50% of the $CaSiO_3$ particles are less than 10 microns in diameter and substantially all the particles are less than 40 microns in diameter, with at least 80% being less than 20 microns in diameter. More specifically, the calcium meta silicate may comprise 99-100% particles having diameters less than 40 microns, 96-100% having diameters less than 30 microns, 93-100% having diameters less than 25 microns, 81-99% having diameters less than 20 microns, 68-91% having diameters less than 15 microns, 48-72% having diameters less than 10 microns, 20-34% having diameters less than 5 microns, and 3-7% having diameters less than 2 microns. Other chemical and physical properties of calcium meta silicate include an acicular crystalline structure, a specific gravity of 2.9, a refractive index of 1.63, a melting point of 1540° C, a hardness value of 4.5 on Moh's scale, a weight of 2.90 kg per solid liter, and a 10% aqueous slurry thereof exhibits a pH of 9.9. Calcium meta silicate has been found to be particularly effective as a dental cleaning and polishing agent without unduly abrading the dental enamel of the teeth.

Wollastonite from Interspace Corporation is a white, natural mineral of substantially pure calcium meta silicate, which may be processed into grades in accordance with particle size.

The presence of the $CaSiO_3$ (Wollastonite) in the dentifrice is found to impart improved tooth polishing and tooth cleaning and stain removal characteristics to the dentifrice.

The proportion of calcium meta silicate in the dentifrice may be at least about 5% and in the range of about 5 to 40%, preferably about 5-32%.

The calcium meta silicate may constitute the sole dental abrasive or may be a part of an abrasive system. Accordingly, either soft or hard dental abrasives may be included. Likewise, a thermoplastic non-abrasive material may be employed. Suitable dental abrasives may be any of those conventionally employed in toothpastes, such as hydrated alumina, anhydrous dicalcium phosphate, calcium pyrophosphate, insoluble sodium metaphosphate, calcium pyrophosphate, insoluble sodium metaphosphate, dicalcium phosphate dihydrate, calcium carbonate, silica of the known high density or intermediate density types (such as those sold under the name Syloid 63 or Syloid 72 or Syloid 74), alkali metal or alkaline earth metal aluminosilicates (such as those having a refractive index of about 1.44-1.47, and containing at least about 70% silica, up to about 10% alumina, up to about 20% by weight of moisture and up to about 10% by weight of sodium oxide, the moisture content preferably being about 10-20% by weight, measured by loss at 1000° C and the typical content of sodium oxide being about 5-10% by weight), kappa-alumina (such as described in U.S. Pat. No. 3,003,919); synthetic resins (such as described in British Pat. No. 995,351); composite abrasive particles in which a hard mineral is coated with, or embedded in, a synthetic resin (the mineral being, for instance, crystalline silica, e.g., quartz, SiC, anhydrous alumina, hematite, zirconium silicate, etc., and the coating being, for instance, an impervious cross-linked thermoset synthetic resin such as melamine-formaldehyde resin, urea-formaldehyde, phenolformaldehyde, or epoxy resins or polymers or copolymers of compounds having two or more polymerizable ethylenically unsaturated groups, e.g., diallyl phthalate polymers, such as described in U.S. Pat. No. 3,151,027).

The dental abrasive may have a particle size about 2 to 40 microns and may also be present in the form of relatively large agglomerates (of the individual particles) of such size as to be visible to the naked eye but easily reduced to the fine impalpable particle size upon being subjected to tooth-brushing in the mouth. Such agglomerates may be agglomerated with or without binding agent which may be water-soluble or water-insoluble.

For most purposes, it is preferable that the said dental abrasive have a particle size less than 20 microns to avoid any gritty feel.

Suitable hard dental abrasives include crystalline silica, calcined alumina, zirconium silicate, $KAlSi_3O_8$, grit (SiC), pumice, ilmenite ($FeTiO_3$), $CeO_2$, $Fe_2O_3$ (hematite), $ZrO_2$, $SnO_2$, and topaz (aluminum hydroxy fluorosilicate).

The hard dental abrasive may have a particle size about 1 to 15 microns and may also be present in the form of easily reducable large agglomerates, similarly to the soft dental abrasives.

The proportion of such additional dental abrasive in the dentifrice may be in the range of 0 to about 30%. Typically, the total polishing agent content is generally in amounts from about 20 to 75% by weight in a dentifrice, and preferably 10 to 50%.

Fine particles of thermoplastic resin may also be present, as a non-abrasive filler material. Such particles of solid polymer have a molecular weight above 1000 (and preferably above 10,000, e.g., about 10,000 to 100,000 or more) and a mean diameter less than about 50 microns (preferably in the range of about 0.5 to 50 microns, e.g., about 10 to 30 microns). The polymer particles may be prepared directly by emulsion or suspension polymerizing or by grinding the polymer in bulk, and may be present in amount of up to about 60% or more of the dentifrice, e.g., in the range of about 20 to 60%, such as about 20 to 50%, e.g., about 30 to 50% in a toothpaste. Examples of thermoplastic resins are polymerized ethylenically unsaturated compounds, such as polyolefines (e.g., polyethylene or polypropylene) or vinyl or vinylidene resins, such as polyvinyl chloride, polystyrene, vinyl chloride-vinyl acetate copolymers, styrene-butadiene copolymers, polyvinylidene chloride; polyamides such as Nylon (e.g., Nylon 6); cellulosics such as cellulose acetate, etc.

To make toothpastes or dental creams, the calcium meta silicate and any other dental abrasives are dispersed in a dental vehicle which preferably contains a liquid which is water and/or humectant such as glycerine, sorbitol, propylene glycol or polyethylen glycol 400, including suitable mixtures thereof. It is usually advantageous to use a mixture of both water and one or two humectants. Polyethylene glycols of higher molecular weight, e.g., polyethylene glycol 600, etc., may also be present. The total liquid content is generally well over 20% by weight of the vehicle (sorbitol, generally present in admixture with water, is considered as a liquid for this purpose). The preferred humectants are glycerine and sorbitol. Typically, the vehicle contains about 0-80% by weight of glycerine, up to about 80% by weight of sorbitol and about 5-80% of water.

The vehicle usually also contains a thickening or gelling agent, such as the natural and synthetic gums and gum-like materials such as Irish Moss, gum tragacanth, alkali metal (e.g., Li, K or Na) carboxymethyl cellulose and hydroxymethyl carboxyethyl cellulose, polyvinyl pyrrolidone, starch, water-soluble hydrophilic colloidal carboxyvinyl polymers such as those sold under the trademark Carbopol 934 and 940, hydroxyethyl cellulose, Indian gum, acacia gum, agar agar, locust bean gum, Laponite CP or SP, which are each synthetic inorganic complex silicate clays sold under trademark by Laporte Industries, Ltd., and pectin or inorganic thickeners such as colloidal silica, e.g., synthetic, finely divided silicas including those sold under the trademarks Cab-O-Sil M5, Syloid 244, Syloid 266, and Aerosil D200. The solid portion of the vehicle is typically present in an amount up to about 10% by weight of the toothpaste and preferably within the range of about 0.5-8% by weight.

The toothpaste may also contain surface-active agent, e.g., to achieve increased prophylactic action, assist in achieving thorough and complete dispersion of the instant compositions throughout the oral cavity, and render the instant compositions more cosmetically acceptable. The organic surface-active material may be anionic, nonionic, amphyolytic, or cationic in nature, and it is preferred to employ as the surface-active agent a detersive material which imparts to the composition detersive and foaming properties. Suitable types of such detergents are water-soluble salts of higher fatty acid monoglyceride monosulfates such as sodium salt of the monosulfated monoglyceride or hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2 hydroxy propane sulfonates, and the substantially saturated higher aliphatic acyl amides of lower aliphatic amino carboxylic acid compounds, such as those having 12 to 16 carbons in the fatty acid alkyl or acyl radicals, and the like. Examples of the last-mentioned amides are N-lauroyl sarcosine, and the sodium, potassium and ethanolamine salts of N-lauroyl, N-myristoyl or N-palmitoyl sarcosinates, which should be substantially free from soap or similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid in the oral cavity due to carbohydrates, in addition to exerting some reduction in the solubility of tooth enamel in acid solutions.

Other suitable surface-active materials include nonionic agents such as condensates of sorbitan monostearate with approximately 60 moles of ethylene oxide, condensates of ethylene oxide with propylene oxide condensates of propylene glycol ("Pluronics") and cationic surface-active germicides and antibacterial compounds such as di-isobutylphenoxyethyldimethyl benzyl ammonium chloride, benzyl dimethyl stearyl ammonium chloride, tertiary amines having one fatty alkyl group (of from 12 to 18 carbon atoms) and two (poly) oxyethylene groups attached to the nitrogen (typically containing a total of from about 2 to 50 ethenoxy groups per molecule) and salts thereof with acids, and compounds of the structure:

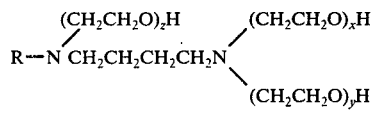

where R is a fatty alkyl group containing from about 12 to 18 carbon atoms, and x, y and z total 3 or higher, as well as salts thereof with mineral organic acids, may also be used. It is preferred that the total amount of surface-active agent be about 0.05-5% by weight, preferably about 1-3% of the dentifrice.

Various other materials may be incorporated in the oral preparation of this invention. Examples thereof are coloring or whitening agents such as titanium dioxide, preservatives, silicones, chlorophyl compounds, ammoniated materials, such as urea, diammoniumphosphate and mixtures thereof, and other constituents. Each of these adjuvants may be typically incorporated in the instant toothpastes in amounts up to about 5%.

The toothpaste may also contain antibacterial agents in amounts of about 0.01–5%. Typical examples of such agents are guanidines, biguanidines and amines such as:

$N^1$-(4-chlorobenzyl-$N^5$-2,4-(dichlorobenzyl)biguanide;

p-chlorophenyl biguanide;

4-chlorobenzhydryl biguanide;

4-chlorobenzhydrylguanylurea;

$N^1$-3-lauroxypropyl-$N^5$-p-chlorobenzylbiguanide;

1,6-di-p-chlorophenylbiguanidohexane;

1-(lauryldimethylammonium)-8-(p-chlorobenzyl-dimethylammonium) octane dichloride;

5,6-dichloro-2-guanidinobenzimidazole;

$N^1$-p-chlorophenyl-$N^5$-laurylbiguanide;

5-amino-1, 3-bis (2-ethylhexyl)-5-methylhexahydropyrimidine; and their non-toxic acid addition salts.

Suitable flavoring or sweetening sialagogues may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram cinnamon, lemon and orange, as well as methyl salicylate. Suitable sweetening agents include sucrose, lactose, maltose, sorbitol, sodium cyclamate and saccharin. Suitably, flavor and sweetening agent may together comprise from about 0.01 to 5% or more of the compositions of the instant invention.

The compositions of the present invention suitably may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride, ($SnF_2.KF$) sodium hexafluorostannate, stannous chlorofluoride, sodium fluorozirconate and sodium monofluorophosphate. These materials, which disassociate or release fluorine-containing ions in water, suitably may be present in an effective but non-toxic amount, usually within the range of about 0.01 to 1% by weight of the water-soluble fluorine content thereof.

The dentifrice may be prepared by suitably mixing the ingredients. For instance, in making a toothpaste, a gelling agent such as sodium carboxymethyl cellulose or Carbopol 934 and a preservative such as sodium benzoate, if employed, is dispersed with a humectant such as glycerine. Water may also be present. Additional humectant and water, as an aqueous 70% sorbitol solution, may then be mixed with the dispersion and a paste, gel or cream is formed. Dental abrasive agent, surface-active agent and flavor are then added. The toothpaste is then thoroughly deaerated (e.g., in vacuo) and tubed . . .

Preferably the amount of water-insoluble essential flavoring oil is above 0.5% and below 2%. Strongly flavored toothpastes contain above 1% of such flavoring oils, e.g., about 1.2 to 1.5%

Instant formulations can be used as prophylactic dental pastes applied professionaly, preparations for use on dentures and for daily use on the teeth.

The following examples are given to illustrate this invention further. In this application all proportions are by weight unless otherwise indicated.

DENTAL CREAM FORMULATIONS

| Constituent: | EXAMPLE 1 % | EXAMPLE 2 % |
|---|---|---|
| Glycerine | 25.0 | 25.0 |
| Sodium carboxymethylcellulose | 1.4 | 1.4 |
| Sodium benzoate | 0.5 | 0.5 |
| Sodium saccharinate | 0.2 | 0.2 |
| $TiO_2$ | 0.4 | 0.4 |
| Water dionized | 32.0 | 33.0 |
| Sodium lauryl sulfate | 1.5 | 1.5 |
| Flavor K91-2962 | 1.0 | 1.0 |
| $SiO_2$, (precipitated hydrated silica thickener) | 6.0 | 7.0 |
| $CaSiO_3$, Wollastonite P-4 (Interpace) | 32.0 | 20.0 |
| $Al_2O_3$, 3 micron Microgrit (Geoscience) | — | 10.0 |

The Wollastonite P-4 has a mean particle size of 10.2 microns, 99% thereof being less than 40 microns, 96% thereof being less than 30 microns, 93% being less than 25 microns, 81% thereof being less than 20 microns, 68% thereof being less than 15 microns, 48% thereof being less than 10 microns, 20% thereof being less than 5 microns, and 3% thereof being less than 2 microns.

These dental creams provide levels of enamel abrasivity and dental abrasivity which are not excessive for regular dental use. They also effectively reduce strain artificially applied to dental surfaces.

A method for determining enamel abrasion levels (REA) for the agents is as follows: Molar teeth are exposed to neutron radiation whereby a predetermined portion of phosphate content is converted to $P^{32}$. Each enamel specimen is mounted in a self-curing polymer such as methyl methacrylate. The specimens are then placed in the specially designed apparatus consisting essentially of a means of stabilizing the enamel specimen, a tube to contain the diluted toothpaste and a toothbrush head under a tension of 150 grams. The enamel specimen is then subjected to 4500 reciprocal brush strokes over the cusped surface. A 2.0 ml aliquot is placed in a planchet dried at room temperature, and the radioactivity ($P^{32}$) determined using a conventional Geiger-Mueller detector. By comparing the radioactivity of the slurries of the experimental pastes to that obtained on each enamel specimen with a reference calcium pyrophosphate powder and which is arbitrarily assigned an enamel abrasion source of 500, the relative abrasiveness of the experimental pastes may be determined.

The dentin abrasion levels (RDA) may be suitably determined using the dentin portions separated from human cuspids and subjecting said dentin to 1000 reciprocal brush strokes. This radioactive technique is more fully described in the literature; Stookey, C. K. and Muhler, J. C., J. Dental Research, 47, 524–538 (1968). Similarly to the REA values, the dentin abrasion should likewise not be high in order to prevent or minimize oral hard tissue damage.

EXAMPLE 3

Example 1 is repeated except that Wollastonite P-15 is used which is a calcium meta silicate having a mean particle diameter of 6.9 microns, all of the particles having a diameter of less than 25 microns, 99% having a diameter less than 20 microns, 91% having a diameter less than 15 microns, 72% having a diameter less than 10 microns, 34% having a diameter less than 5 microns and 7% having a diameter less than 2 microns, is substituted for the larger particle size calcium meta silicate. This dental cream has acceptable dentin and enamel abrasivity levels and reduces artificially applied dental stain.

EXAMPLE 4

Example 3 is repeated except that the calcium meta silicate is reduced to 5%, and 20% hydrated silica and 10% alumina having a mean particle diameter of 3 microns are added, and the water content is adjusted accordingly. This dental cream has acceptable dentin abrasivity.

EXAMPLE 5

Example 4 is repeated except that 8% alumina having a mean particle diameter of 5 microns is substituted for the 10% of 3 micron alumina and the water content is adjusted. This dentifrice has acceptable enamel and dentin abrasivity.

EXAMPLE 6

Example 2 is repeated except that 24% $CaSiO_3$ having a mean particle size of 6.9 microns as in Example 3 is substituted for the $CaSiO_3$ content and the water is adjusted accordingly. This dentifrice has acceptable dentin and enamel abrasivity levels and reduces artificially formed stain.

EXAMPLE 7

Example 6 is repeated but the $CaSiO_3$ is reduced to 20% and the alumina is increased to 15%. This dentifrice has acceptable enamel and dentin abrasivity.

EXAMPLE 8

Example 7 is repeated except that the $CaSiO_3$ is reduced to 15% and the water content adjusted. This dentifrice has acceptable enamel and dentin abrasivity levels and reduces artificially applied dental stain.

EXAMPLE 9

Example 7 is repeated except that a $CaSiO_3$ having a mean particle size of 10.2 microns as defined in Example 1 is used. This dentifrice has acceptable enamel and dentin abrasivity levels and reduces artificially applied dental stain.

EXAMPLE 10

Example 2 is repeated, but the grade of $CaSiO_3$ used is Wollastonite P-15 as defined in Example 3. This dental cream has acceptable enamal and dentin abrasivity.

EXAMPLE 11

Example 8 is repeated except that a different grade $CaSiO_3$ is used, namely Wollastonite P-4 as defined in Example 1. This dentifrice has acceptable enamel and dentin abrasivity.

EXAMPLE 12

Example 11 is repeated except that 5% $NaHCO_3$ is added and the water content is adjusted accordingly. This dentifrice has acceptable enamel and dentin abrasivity levels and reduces artificially applied dental stain.

| DENTAL CREAM FORMULATIONS | | |
|---|---|---|
| Constituent | EXAMPLE 13 % | EXAMPLE 14 % |
| Glycerine | 22.0 | 22.0 |
| Sodium carboxymethyl cellulose | 0.85 | 0.85 |
| Sodium benzoate | 0.5 | 0.5 |
| Sodium saccharinate | 0.2 | 0.2 |
| Water | 29.15 | 29.15 |
| $CaSiO_3$ (Wollastonite P-4) | 5.0 | 10.0 |
| Polyvinylchloride | 40.0 | 35.0 |
| Flavor | 0.8 | 0.8 |
| Sodium lauryl sulfate | 1.5 | 1.5 |

These dentifrices have acceptable enamel abrasivity levels and indicate that suitable compositions can be formulated containing as little as 5% calcium meta silicate as the polishing agent.

The particle size of the $CaSiO_3$ can be an important factor in the abrasivity of the resultant dentifrice. A calcium meta silicate having substantially all of its particles less than 40 microns in diameter, at least 80% thereof less than 20 microns in diameter, and at least 50% less than 10 microns in diameter, is effective in producing a desirable abrasivity and stain removal characteristics in a dentifrice.

It is also within the broader scope of the invention to include other abrasives such as sodium aluminosilicate, calcium phosphates, carbonates, and other aforementioned abrasives.

While the calcium meta silicate has proved most useful thus far in dental creams, they may also be similarly incorporated into toothpowders.

The pH of the dentifrices is generally within the range of about 6 to 10, e.g., about 8 to 10. In the case of a dental cream the pH is typically determined in a 20% slurry.

The particle diameters given in the examples are determined by conventional methods. Thus, the standard liquid sedimentation technique may be used. The calculation of particle diameter from the sedimentation data being made (as is conventional) on the basis of Stokes' Law, disregarding the particular shape of the particles.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

What is claimed is:

1. A dentifrice toothpaste preparation containing as the essential cleaning and polishing agent, about 5 to about 40% of calcium meta silicate in the form of Wollastonite particles having a hardness value of about 4.5 on Moh's scale, and having a mean diameter in the range of about 2 to 15 microns, and composed of about 50.9% $SiO_2$ and about 46.9% CaO dispersed in a dental cream toothpaste vehicle.

2. A dentifrice in accordance with claim 1, wherein the vehicle contains about 10-50% polishing agent.

3. A dentifrice in accordance with claim 1, wherein said calcium meta silicate is present in an amount of about 32% by weight and is the sole polishing agent.

4. A dentifrice in accordance with claim 1, wherein the calcium meta silicate constitutes about 5-32% by weight of the total.

5. A dentifrice in accordance with claim 4, wherein substantially all of the calcium meta silicate particles are less than 40 microns in diameter, at least 80% thereof are less than 20 microns in diameter, and at least 50% thereof are less than 10 microns in diameter.

6. A dentifrice in accordance with claim 5, in which the calcium meta silicate has a mean particle diameter of 10.2 microns.

7. A dentifrice in accordance with claim 5, in which the calcium meta silicate has a mean particle diameter of 6.9 microns.

* * * * *